United States Patent [19]

Dame et al.

[11] Patent Number: 4,707,357

[45] Date of Patent: Nov. 17, 1987

[54] IMMUNOLOGICALLY ACTIVE PEPTIDES CAPABLE OF INDUCING IMMUNIZATION AGAINST MALARIA AND GENES ENCODING THEREFOR

[75] Inventors: John B. Dame, Rockville, Md.; Jackie L. Williams, Universal City, Tex.; Thomas F. McCutchan, Silver Spring; Imogene Schneider, Gaithersburg, both of Md.

[73] Assignee: The United States of America as represented by the Secretary of the Army, Washington, D.C.

[21] Appl. No.: 624,564

[22] Filed: Jun. 26, 1984

[51] Int. Cl.⁴ .................... A61K 37/02; C07K 13/00; C07K 7/10; C07K 7/08; C07K 7/06

[52] U.S. Cl. ...................................... 424/88; 530/350; 530/324; 530/325; 530/326; 530/327; 530/328

[58] Field of Search ...................... 424/88; 260/112 R; 530/350, 324, 325, 326, 327, 328

[56] References Cited

U.S. PATENT DOCUMENTS 4,466,917  8/1984  Nussenzweig et al. ......... 260/112 R
4,554,101  11/1985  Hopp ..................................... 424/88

OTHER PUBLICATIONS

Science, vol. 220, (1983), 1285–1288.
Cell, vol. 34, 815–822, (1983).
Molecular and Biochem. Para. 15, (1985), 305–316.
J. Exp. Med., 157, (1983), 1947–1957.
The Journal of Biol. Chem., 258, No. 5, (1983), 3341–3345.
Biochem., (1984), 23, 5665–5670.
Molecular Parasitology, pp. 127–142, (1984).
Nature, vol. 305 (1983), 29–33.
Phil. Trans. R. Soc. Lond. B., 307, 129–139, (1984).

*Primary Examiner*—Delbert R. Phillips
*Attorney, Agent, or Firm*—John H. Raubitschek; Francis A. Cooch; Werten F. W. Bellamy

[57] ABSTRACT

An immunologically active substantially pure peptide capable of inducing in a human an immune response which is cross reactive with and protective against infection by a malaria parasite, wherein the peptide contains at least 2 consecutive repeats of a sequence Asn-X-Y-Pro wherein X is Ala or Val and Y is Asn or Asp or a sequence of the formula Thr-Glu-Trp-Z-Pro-Cys-Ser-Val-Thr-Cys-Gly-Asn-Gly wherein Z is Ser or Thr or the formula Lys-Pro-S-T-S-Lys-Leu-Lys-Gln-Pro-U-V-Gly-W-Pro wherein S is Lys or Asn, T is His or Glu, U is Gly or Asn, V is As or Glu, and W is Asn or Gln is disclosed along with DNA sequences and various other genetic materials useful in producing these peptides through biological methods.

30 Claims, 4 Drawing Figures

REGION I

P. falciparum ...Lys Pro Lys His Lys Lys Leu Lys Gln Pro Gly Asp Gly Asn Pro Asp Pro Repeats......
                 107                                                      121

P. knowlesi    ...Lys Pro Asn Glu Asn Lys Leu Lys Gln Pro Asn Glu Gly Gln Pro Repeats.........
                 65                                                       102

Fig. 4a

REGION II

P. falciparum ...Thr Glu Trp Ser Pro Cys Ser Val Thr Cys Gly Asn Gly ....
                 344                                            356

P. knowlesi   ...Thr Glu Trp Thr Pro Cys Ser Val Thr Cys Gly Asn Gly .....
                 296                                            308

Fig. 4b

IMMUNOLOGICALLY ACTIVE PEPTIDES CAPABLE OF INDUCING IMMUNIZATION AGAINST MALARIA AND GENES ENCODING THEREFOR

BACKGROUND OF THE INVENTION

1. Field of the Invention

This invention is related to immunologically active agents capable of inducing immune responses in humans and other animals which result in protection against infection by malaria parasites and more particularly to the protection of humans against the human malaria parasite *Plasmodium falciparum*.

2. Description of the Prior Art

The need for vaccines to relieve the current global resurgence of malaria is clear. Because immunity in malaria is stage specific, vaccines are being developed against each stage in the malarial life cycle: sporozoites, the mosquito stage that initiates infection in man; asexual erythrocytic parasites, the stage that causes the disease; and gametes, the stage that transmits the infection to mosquitoes. One area of interest is a sporozoite vaccine which, if effective, would prime the immune system to kill sporozoites innoculated by the mosquito and thus prevent the subsequent stages responsible for the disease in transmission of the infection to others.

Animals and man have previously been protected by injection of irradiated sporozoites. Vaccination with irradiated sporozoites is impractical, however, because of the limited supply and instability of sporozoites. Use of monoclonal antibodies led to the discovery of the major surface protein on sporozoites of *Plasmodium berghei*, a rodent malaria (N. Yoshida, R. S. Nussenzweig, P. Potocnjak, et al, *Science* 207, 71 (1980)). This protein covers the surface of the sporozoite and is referred to as the circumsporozoite (CS) protein. Injection of monoclonal antibodies to the CS protein of *P. berghei* completely protected mice from challenge by infected mosquitoes (P. Potocnjak, R. S. Nussenzweig, V. Nussenzweig, *J. Exp. Med.* 151, 1504 (1980)). Analogous CS proteins have been identified for species of monkey and human malaria, including *P. falciparum*, the major malaria of man (F. Santoro et al, *J. Biol. Chem.* 258, 3341 (1983); E. H. Nardin et al, *J. Exp. Med.* 156, 20 (1982)), although the structure of the *P. falciparum* protein was not known prior to the present invention. The gene for the CS protein of the monkey malaria, *P. knowlesi*, was cloned first because of the availability of large numbers of *P. knowlesi* sporozoites in infected mosquitoes for preparation of a cDNA library J. Ellis (L. S. Ozaki, R. W. Gwadz et al, *Nature* 302, 536 (1983); G. N. Godson, J. Ellis, P. Svee et al, *Nature* 305, 29 (1983)). This gene encoded for a protein with a repeating amino acid sequence (12 amino acids repeated 12 times) which contained the epitope that bound the protective monoclonal antibodies. This repeating epitope was the major immunogen on the protein as monoclonal antibodies blocked access of polyclonal anti-sporozoite sera to Triton X-100 solubilized protein in the immunoradiometric assay (F. Zavala, A. H. Cochrane, E. H. Nardin et al, *J. Exp. Med.* 157, 1947 (1983)).

However, there remains a need for an antigenic material related to the CS protein of a human malaria parasite since antibodies previously prepared against this repeating epitope from monkey parasites are not reactive with human malaria parasites.

SUMMARY OF THE INVENTION

Accordingly, it is an object of this invention to provide a peptide sequence associated with a human malaria antigen which is capable of inducing a protective immune response in humans.

It is another object of this invention to provide a DNA sequence capable of expressing antegenic material having such characteristics.

These and other objects of the invention as will hereinafter become more readily apparent have been accomplished by providing an immunologically active substantially pure peptide capable of inducing in a human an immune response either alone or when attached to a carrier molecule which is cross reactive with and protective against infection by a malaria parasite, wherein said peptide contains at least 2 consecutive repeats of a sequence Asn-X-Y-Pro wherein X is Ala or Val and Y is Asn or Asp. Similar protection can be achieved if the peptide contains a sequence of the formula Thr-Glu-Trp-Z-Pro-Cys-Ser-Val-Thr-Cys-Gly-Asn-Gly wherein Z is Ser or Thr or the formula Lys-Pro-S-T-S-Lys-Leu-Lys-Gln-Pro-U-V-Gly-W-Pro wherein S is Lys or Asn, T is His or Glu, U is Gly or Asn, V is Asp or Glu, and W is Asn or Gln.

The invention also includes genetic materials useful in the production of such peptides in biological systems, such as the DNA sequences which code for the object peptides.

BRIEF DESCRIPTION OF THE DRAWINGS

A more complete appreciation of the invention and many of the attendant advantages thereof will be readily obtained by reference to the following detailed description when considered in connection with the accompanying drawings, wherein:

FIG. 2 shows the nucleotide sequence of the CS protein gene from *P. falciparum*. The nucleotide sequence of the CS protein gene in λmPf1 is shown. The EcoR1 insert in λmPf1 was subcloned in pUC8 and then sequenced. The sequence of both DNA strands was determined for 100% of the CS protein coding region and greater than 70% of the flanking regions. The inserts of clones λmPf5, 8, 13 and 15 were also subcloned into pUC8 and the ends sequenced. The first base of each clone 5' to the CS protein coding region is located to the right of the arrows. The EcoR1 linkers (GGAATTCC) ligated at both ends of the inserts are not shown as part of the sequence. The deduced amino acid sequence of the CS protein is given beneath the nucleotide sequence. Two regions of the protein from *P. falciparum* homologous to the *P. knowlesi* CS protein are marked Region I and Region II. The repeat units are underlined, and the variant amino acids in the units are within boxes. The amber terminator codon in the sequence is indicated with stars.

DESCRIPTION OF THE PREFERRED EMBODIMENTS

All publications or patents hereafter mentioned in this specification are herein incorporated by reference.

The present invention arose in part from the discovery of the properties and structure of the immunologically active segments of the CS protein from P. falciparum. The inventors have confirmed that monoclonal antibodies reactive with the CS protein of P. falciparum are directed against repeating units found in the protein. Now that these repeating units (and other regions of the CS protein which appear to be invariant regions found in several plasmodium species) have been identified, it is possible to produce, by either synthetic chemical means or by biological means, peptides containing these immunodominant regions which form the basis for vaccines.

Accordingly, the present invention comprises an immunologically active substantially pure synthetic peptide capable of inducing in a human an immune response either alone or when attached to a carrier molecule which is cross reactive with and protective against infection by a malaria parasite, wherein said peptide contains at least 2 consecutive repeats of a sequence Asn-X-Y-Pro wherein X is Ala or Val and Y is Asn or Asp or a sequence of the formula Thr-Glu-Trp-Z-Pro-Cys-Ser-Val-Thr-Cys-Gly-Asn-Gly wherein Z is Ser or Thr or the formula Lys-Pro-S-T-S-Lys-Leu-Lys-Gln-Pro-U-V-Gly-W-Pro wherein S is Lys or Asn, T is His or Glu, U is Gly or Asn, V is Asp or Glu, and W is Asn or Gln. Accordingly, there are at least three variations of peptides which have the desired immunological character: (1) a peptide which contains the repeating units but not the longer sequences; (2) a peptide which contains one or both of the two longer sequences (often referred to herein as Region I and Region II, respectively, in this application); and (3) a peptide containing both the repeating units and one or both of the sequences identified as Region I and Region II.

The term "synthetic" as used herein is intended to indicate that the previously known CS protein from P. falciparum is specifically excluded from peptides of this invention when in its natural state. The present invention rests in part of the discovery of the structure of the epitopes of the CS protein and on the ability of antibodies against these epitopes to produce immunity against malaria. Once the structure of the epitope became known, it became possible to design synthetic peptides useful as vaccines. Synthetic here does not, however, exclude production by biological methods in which human have intervened, for example by genetic engineering.

One key characteristic of all peptides of the invention is that they are immunologically active and are capable of inducing a human response which is cross reactive against infection by a malaria parasite either alone or when attached to a carrier molecule. Accordingly it is necessary that at least part of the enumerated sequences be present on an immunogenically available surface of a peptide containing one or more of these sequences. Several methods are available for designing a peptide having these characteristics.

First, it is possible to chemically or biochemically synthesize a peptide in which the peptides consist essentially of the enumerated sequences. Such peptides would contain at least 10% of their amino acids in the enumerated sequences, preferably at least 40%, more preferably at least 60%, and most preferably at least 80%. Most preferred are peptides which consist entirely of the enumerated sequences (along with peptides which can be considered as consisting of the enumerated repeat sequence in which 1-3 terminal amino acids of the peptide are missing from either or both ends of the peptide).

It is also possible to design peptides in which the enumerated sequences of amino acids are found on the surface of the final peptide. This can be done, for example, by attaching one or more of the enumerated sequences to a surface of a previously prepared peptide by means of a peptide bond.

However, even in the event that one or more of the enumerated sequences is contained within the interior of the amino acid sequence of a larger synthetic peptide or protein, those skilled in the art of immunology can readily determine if the peptide falls within the scope of the present invention. Only those peptides which are reactive with antibodies raised against CS proteins are considered to be within the scope of the present invention. Accordingly, one skilled in the art may readily synthesize a peptide containing one of the sequences of the present invention and then determine by routine testing whether or not the finished product is within the scope of the present invention by reacting the protein with an antibody (preferably a monoclonal antibody) raised againt a CS protein, preferably a CS protein of P. falciparum, or against a peptide consisting essentially or entirely of one of the sequences specifically set forth in this application. If a positive immunological reaction takes place, the protein falls within the scope of the present invention. Antibodies reactive with the CS protein of P. falciparum are public and readily available, for example being produced by deposited hybridoma cell line ATCC HB8583, which produces the antibody identified herein as 49.2F1.1.

There is no upper limit on the size of molecules of the invention, other than those limits set by the ability to synthesize large peptide molecules. Molecules of the invention can be either soluble or insoluble in aqueous solutions. In fact, one preferred embodiment of the invention involves the synthesis of high molecular weight, insoluble peptides which can be ground and injected as an aqueous suspension in order to induce immunological protection. Nevertheless, smaller molecules are also suitable for carrying out the invention. Molecules containing 100, 200, 400, or even 1,000 repeat units are suitable for the practice of the present invention. However, there appears to be no necessity of synthesizing peptides containing more than fifty repeat units since peptides containing up to fifty repeat units will be sufficient to induce the desired immunological effect and are easier to synthesize. Molecules with 20 to 50 repeat units are particularly preferred. Peptides which contain up to 50 repeat units in which the repeat units from at least 40%, more preferably 80%, of the entire peptide are preferred. Of the possible repeat units, Asn-Ala-Asn-Pro is most preferred with the repeat unit Asn-Val-Asp-Pro being the second most preferred sequence. Peptides in which at least 80% of the repeating units are Asn-Ala-Asn-Pro with the remainder being Asn-Val-Asp-Pro are particularly preferred.

One especially preferred peptide sequence for peptides containing the repeat units is a peptide which consists essentially of the sequence A-B-A-B-A-B-$(A)_{15}$-B-$(A)_x$ wherein A represents Asn-Ala-Asn-Pro, B represents Asn-Val-Asp-Pro, and x is 0–30, preferably 15–25, and most preferably 20.

When a peptide of the invention contains one of the sequences not listed specifically as a required repeating sequence (although of course these sequences may repeat if desired), peptides in which Z is Ser, S is Lys, T is His, U is Gly, V is Asp, and W is Asn are preferred. Of the two enumerated longer sequences, peptides containing the sequence Thr-Glu-Trp-Z-Pro-Cys-Ser-Val-Thr-Cys-Gly-Asn-Gly (i.e., Region II) are preferred.

When a peptide of the invention is synthesized containing both the repeat sequences and one or more of the peptide sequences identified as Region I or Region II, those peptides which are preferred contain from 2 to 50 of the repeating units followed by a peptide sequence containing the sequence of Region II and preceded by a peptide sequence containing the sequence of Region I. A particularly preferred peptide contains a sequence of the formula Lys-Pro-Lys-His-Lys-Lys-Leu-Lys-Gln-Pro-Gly-Asp-Gly-Asn-Pro-Asp-Pro-Asn-Ala-Asn-Pro-Asn-Val-Asp-Pro-Asn-Ala-Asn-Pro-Asn-Val-Asp-Pro-Asn-Ala-Asn-Pro-Asn-Val-Asp-Pro-Asn-Ala-Asn-Pro-Asn-Ala-Asn-Pro-Asn-Ala-Asn-Pro-Asn-Ala-Asn-Pro-Asn-Ala-Asn Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Val-Asp-Pro-Asn-Ala-Asn-Pro-Asn-Ala-Asn-Pro-Asn-Ala-Asn-Pro-Asn-Ala-Asn-Pro-Asn-Ala-Asn Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Ans-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Lys-Asn-Asn-Gln-Gly-Asn Gly-Gln-Gly-His-Asn-Met-Pro-Asn-Asp-Pro-Asn-Arg-Asn-Val-Asp-Glu-Asn-Ala-Asn-Ala-Asn-Asn-Ala-Val-Lys-Asn-Asn-Asn-Asn-Glu-Glu-Pro-Ser-Asp-Lys-His-Ile-Glu-Gln-Tyr-Leu-Lys-Lys-Ile-Lys-Asn-Ser-Ile-Ser-Thr-Glu-Trp-Ser-Pro-Cys-Ser-Val-Thr-Cys-Gly-Asn-Gly.

The preferred method of synthesizing peptides of the invention containing repeat units is formation of one or more tetramer of the desired structure followed by polymerization of the tetramers to produce the final product. Very large peptides can be produced in this manner. Such chemical synthesis is also preferred when a long repeat sequence is present as part of a larger molecule. The repeating sequence and the shorter variable sequences can be synthesized independently and then joined to produce the desired final products. Such techniques are well within the skill of those knowledgeable in peptide synthesis. For example, U.S. Pat. No. 4,132,746 describes the synthesis of peptide tetramers and the polymerization of the tetramers to form larger molecules. The method described therein can easily be adapted to the present invention by selecting the amino acids described herein instead of the amino acids listed in the patent.

Of course, with the advent of modern peptide synthesizers, many of which are available commercially, it has been increasingly easier to synthesize either complete large peptide molecules or synthesize large fragments which can then be joined in turn.

Before a description of the genetic (biological) methods of synthesizing peptides of the invention is given, it will be useful to consider a preferred embodiment of the invention in which the ability of peptides of the invention to induce immunological response is enhanced by bonding one or more of the peptides of the invention to an immunogenic carrier. The resulting product, having enhanced immunogenicity, is referred to herein as an antimalarial immunogenic stimulant.

The use of immunogenic carriers to enhance the immunogenicity of small molecules is well known. Carriers are basically divided into two classes, soluble molecules and particles. Typical examples of soluble molecules are proteins and polysaccharides. Typical examples of particles are liposomes and bacterial cells or parts thereof, such as membranes. Whole cells are generally killed or their reproduction is hindered in order to avoid problems associated with infection.

In all cases, the actual structure of the carrier is unimportant since it is the size of the carrier which acts to increase the immunogenic response. When soluble macromolecules, such as proteins and polysaccharides, are used as carriers, molecular weights in the range of 10,000 to 1,000,000 are preferred. If sufficiently large, the protein or polysaccharide carrier may be insoluble and thus be considered to be a particulate material.

The method of attaching a peptide to the carrier is relatively unimportant so long as the immunogenic specificity of the peptide is retained at least in part. A preferred method of achieving this result is to attach a peptide to the carrier by means of an amide bond formed between a carboxylic acid or amino group of the carrier and an amino or carboxylic acid group of the peptide, particularly a free carboxylic acid or amino terminal group of the peptide. Another preferred method of bonding is the formation of an ester bond between a carboxylic acid or hydroxy group of the carrier and an hydroxy or carboxylic acid group of the peptide, preferably a terminal carboxylic acid group of the peptide. Linking groups, e.g. terminal diamines with 1 to 10 methylene carbons joining the amines, can be used if desired.

When a carrier is used, the immunogenic response can be enhanced by bonding multiple peptides to the surface of the carrier. For example, from 1 to 100,000 peptides can be bound to a protein or polysaccharide with 100 to 10,000 being preferred. When proteins are used as a carrier, amphoteric proteins are preferred. Such proteins have a liphophilic portion and a hydrophilic portion. In such proteins, it is preferred to attach peptides of the invention to the hydrophilic region, thereby exposing them to the humoral environment when the lipophilic region becomes embedded in various membranes.

One preferred protein for use as a carrier is tetanus toxoid, a routinely used vaccine which is a material previously suggested for use as an immunogenic carrier.

The preferred embodiments listed above for use with macromolecule carriers also apply for use with particulate carriers except that the upper limit of peptides per carrier is approximately $10^{15}$, preferably $10^{10}$. Bacterial cells (killed or otherwise hindered from reproducing) are the preferred particulate materials.

When peptides which closely resemble the native CS protein from *P. falciparum* are desired, it is preferable to synthesize the peptide biologically using a gene associated with or derived from the CS protein gene of *P. falciparum*. The resulting gene products can then be modified, for example by cleavage of terminal amino acids.

The advent of the recombinant DNA technology has lead to a recent and rapid increase in the number of techniques available for producing cloned gene products. Examples of recent U.S. patents which describe methods suitable for producing cloned genes suitable for use in the present invention include U.S. Pat. Nos. 4,419,450, 4,418,194, 4,414,150, 4,399,216, 4,394,443, 4,356,270, 4,351,901, and 4,237,224. Of course, it is also possible to modify the techniques described therein by synthesizing DNA sequences capable of expressing the desired peptide product and inserting them into suitable cloning vectors as described in U.S. Pat. Nos. 4,273,875, 4,304,863, 4,332,901, 4,403,036, 4,363,877, and 4,349,629. The following description describes genetic engineering procedures in general which are suitable for use with this invention.

Genetic information is encoded on double-stranded deoxyribonucleic acid ("DNA" or "genes") according to the order in which the DNA coding strand presents the characteristic bases of its repeating nucleotide components. "Expression" of the encoded information to form polypeptides involves a two-part process. According to the dictates of certain control regions ("regulons") in the gene, RNA polymerase may be caused to move along the coding strand, forming messenger RNA (ribonucleic acid) in a process called "transcription." In a subsequent "translation" step the cell's ribosomes in conjunction with transfer RNA convert the mRNA "message" into polypeptides. Included in the information mRNA transcribes from DNA are signals for the start and termination of ribosomal translation, as well as the identity and sequence of the amino acids which make up the polypeptide. The DNA coding strand comprises long sequences of nucleotide triplets called "codons" because the characteristic bases of the nucleotides in each triplet or codon encode specific bits of information. For example, 3 nucleotides read as ATG (adenine-thymine-guanine) result in an mRNA signal interpreted as "start translation", while termination codons TAG, TAA and TGA are interpreted "stop translation". Between the start and stop codons lie the so-called structural gene, whose codons define the amino acid sequence ultimately translated. That definition proceeds according to the well-established "genetic code" (e.g., J. D. Watson, Molecular Biology of the Gene, W. A. Benjamin Inc., N.Y., 3rd ed. 1976) which describes the codons for the various amino acids. The genetic code is degenerate in the sense that different codons may yield the same amino acid, but precise in that for each amino acid there are one or more codons for it and no other. Thus, for example, all of the codons TTT, TTC, TTA and TTG, when read as such, encode for serine and no other amino acid. During translation the proper reading phase or reading frame must be maintained. Consider for example what happens when the ribosome reads different bases as the beginning of a codon (underlined) in the sequence . . . GCTGGTTGTAAG . . . :

. . . <u>GCT</u> <u>GGT</u> <u>TGT</u> <u>AAG</u> . . . → . . . Ala—Gly—Cys—Lys . . .

G <u>CTG</u> <u>GTT</u> <u>GTA</u> AG . . . → . . . Leu—Val—Leu . . .

. . . GC <u>TGG</u> <u>TTG</u> <u>TAA</u> A . . . → . . . Trp—Leu—(STOP).

The polypeptide ultimately produced, then, depends vitally upon the spatial relationship of the structural gene with respect to the region.

A clearer understanding of the process of genetic expression will emerge once certain components of genes are defined:

Operon—A gene comprising structural gene(s) for polypeptide expression and the control region ("regulon") which regulates that expression.

Promoter—A gene within the regulon to which RNA polymerse must bind for initiation of transcription.

Operator—A gene to which repressor protein may bind, thus preventing RNA polymerase binding on the adjacent promoter.

Inducer—A substance which deactivates repressor protein, freeing the operator and permitting RNA polymerase to bind the promoter and commence transcription.

Catabolite Activator Protein ("CAP") Binding Site—A gene which binds cyclic adenoisine monophosphate ("cAMP")-mediated CAP, also commonly required for initiation of transcription. The CAP binding site may in particular cases be unnecessary. For example, a promoter mutation in the lactose operon of the phage λplac UV5 eliminates the requirement for cAMP and CAP expression. J. Beckwith et al, *J. Mol. Biol.* 69, ISS-160 (1972).

Promoter-Operator System—As used herein, an operable control region of an operon, with or without respect to its inclusion of a CAP binding site or capacity to code for repressor protein expression.

Further by way of definition, and for use in the discussion of recombinant DNA which follows, we define the following:

Cloning Vehicle—Non-chromosomal double stranded DNA comprising an intact "replicon" such that the vehicle is replicated, when placed within a unicellular organism ("microbe") by a process of "transformation". An organism so transformed is called a "transformant".

Plasmid—For present purposes, a cloning vehicle derived from viruses or bacteria, the latter being "bacterial plasmids."

Complementarity—A property conferred by the base sequences of single strand DNA which permits the formation of double standard DNA through hydrogen bonding between complementary bases on the respective strands. Adenine (A) complements thymine (T), while guanine (G) complements cytosine (C).

Advances in biochemistry in recent years have led to the construction of "recombinant" cloning vehicles in which, for example, plasmids are made to certain exogenous DNA. In particular instances the recombinant may include "heterologous" DNA, by which is meant DNA that codes for polypeptides ordinarily not produced by the organism susceptible to transformation by the recombinant vehicle. Thus, plasmids are cleaved to provide linear DNA having ligatable termini. These are bound to an exogenous gene having ligatable termini to provide a biologically functional moiety with an intact replicon and a desired phenotypical property. The recombinant moiety is inserted into a microorganism by transformation and transformants are isolated and cloned, with the object of obtaining large populations capable of expressing the new genetic information. Methods and means for forming recombinant cloning vehicles and transforming organisms with them have been widely reported in the literature. See, e.g., H. L. Heynecker et al, *Nature* 263, 748–752 (1976); Cohen et al, *Proc. Nat. Acad. Sci.* USA 69, 2110 (1972); ibid., 70, 1293 (1973); ibid., 70, 3240 (1973); ibid., 71, 1030 (1974); Morrow et al, *Proc. Nat. Acad. Sci.* USA 71, 1743 (1974) and Jackson et al, ibid, 69, 2904 (1972). A generalized discussion of the subject appears in S. Cohen, *Scientific American* 233,24 (1975). These and other publications alluded to herein are incorporated by reference.

A variety of techniques are available for DNA recombination, according to which adjoining ends of separate DNA fragments are tailored in one way or another to facilitate ligation. The latter term refers to the formation of phosphodiester bonds between adjoining nucleotides, most often through the agency of the enzyme T4 DNA ligase. Thus, blunt ends may be directly ligated. Alternatively, fragments containing complementary single strands at their adjoining ends are advantaged by hydrogen bonding which positions the respective ends for subsequent ligation. Such single strands, referred to as cohensive termini, may be formed by the addition of nucleotides to blunt ends using terminal transferase, and sometimes simply by chewing back one strand of a blunt end with an enzyme such λ-exonuclease. Again, and most commonly, resort may be had to restriction endonucleases, which cleave phosphodiester bonds in and around unique sequences of nucleotides of about 4–6 base pairs in length. Many restriction endonucleases and their recognition sites are known, the so-called Eco RI endonuclease being most widely employed. Restriction endonucleases which cleave double-stranded DNA at rotationally symmetric "palindromes" leave cohesive termini. Thus, a plasmid or other cloning vehicle may be cleaved, leaving termini each comprising half the restriction endonuclease recognition site. A cleavage product of exogenous will have ends complementary to those of the plasmid termini. Alternatively, as disclosed infra, synthetic DNA comprising cohesive termini pending insertion of exogenous DNA, the termini can be digested with alkaline phosphatase, providing molecular selection for closures incorporating the exogenous fragment. Incorporation of a fragment having the proper orientation relative to other aspects of the vehicle may be enhanced when the fragment supplants vehicle DNA excised by two different restriction endonucleases, and itself comprises termini rspectively constituting half the recognition sequence of the different endonucleases.

One method for producing the entire CS protein is described in the following general method. This method relies on the use of the mung bean nuclease under controlled conditions of formamide concentration and temperature to preferentially cut the 5' and 3' end of genes. DNA fragments obtained in this manner can be cloned into various expression vectors, such as the vector λgt11. Clones produced, for example by transformation with a cloning vehicle, are screened by expression with antibody against the CS protein. The present invention accordingly includes a substantially pure DNA sequence coding for a peptide which has previously been described. Such DNA sequences can readily be synthesized using automated equipment which is now commercially available. The actual DNA sequence can readily be calculated from the amino acid sequences previously given. Particularly preferred DNA sequences comprise fragments derived from the DNA sequence set forth in FIG. 2. Especially preferred are those DNA sequences which correspond, according to the correspondence shown in FIG. 2, to the amino acid sequences which have previously been described herein as preferred.

A recombinant cloning vehicle containing one of these DNA sequences is also included within the scope of the present invention. This cloning vehicle may be a microbial or yeast plasmid or a bacteriophage. One particularly preferred cloning vehicle is λgt11. A unicellular organism containing a DNA sequence as discussed above which is capable of expressing an immunologically active peptide capable of inducing in a human an immune response which is cross reacted with and protective against a malarial parasite is accordingly included within the scope of the present invention when the DNA sequence has been artificially introduced into the unicellular organism. *E. coli* are preferred hosts.

This invention is exemplified by several deposits which have been made with the American Type Culture Collection, Rockville, Md. The microorganisms identified as lambda-mPf1, 3, 5, 8, 11, and 13 are respectively identified by the following ATCC deposit numbers 39738, 39739, 39740, 39741, 39742, 39743, and 39744.

Although genetic material for use in the practice of this invention can be synthetically produced as discussed above, it is also possible to derive suitable genetic material directely from *P. falciparum* protezoa using known techniques. Among the publically available *P. falciparum* protozoa is the one identified as 7G8 which is deposited with the American Type Culture Collection under the deposit number ATCC 40123.

The invention also includes a method for inducing immunization against malaria which comprises administering an immunologically effective amount of a peptide of the invention to a human. The appropriate therapeutically effective dose can be determined readily by those skilled in the art and will usually be in the range from about 0.01 μg/kg to about 100 μg/kg of body weight. More preferably, the dosage is in the range of from 0.1 to about 1.0 μg/kg.

The mode of administration of peptides of the invention may be by any suitable route which delivers the peptide to the immunological system. For the purposes of the present invention, the peptide may be administered intramuscularly, interveneously, or by any other method which enables the active ingredient to reach lymphocytes and induce an immune response.

Peptides of the invention may be prepared into pharmaceutical compositions containing the active ingredient in a form suitable for inducing an immune response. Aqueous suspensions or solutions containing the active material in a form ready for injection are preferred. Adjuvants can be used to enhance the immune response if desired.

It is preferred that the peptides of the invention, when the form of pharmaceutical preparations, are present in unit dosage forms. When intended for human use, these amounts can easily be calculated from the dosage rates previously given by assuming a body weight of 70 kg. Accordingly, a preferred unit-dose-containing pharmaceutical preparation would contain from about 7 to about 70 µg of active ingredient. It will be understood, however, that the specific dose level for any particular patient will depend upon a variety of factors including the activity of the specific compound employed; the age, general health, sex, and diet of the patient; the time of administration; the route of administration; the rate of excretion; possible synergistic effects with any other drugs being administered; and the degree of protection being sought.

This application uses the standard nomenclature and abbreviations of biochemistry for peptide and DNA sequences. An example publication setting forth the standard nomenclature used in this application for peptide and DNA sequences is Lehninger, *Biochemistry*, Worth publishers, New York, 1970, chapters 4 and 5 (peptides) and 12 (DNA).

The invention now being generally described, the same will be better understood by reference to certain specific examples which are included herein for purpose of illustration only and are not intended to be limiting of the invention or any embodiment thereof, unless specified.

EXAMPLE

Clones from the Genomic DNA Expression Library

The *P. falciparum* genomic DNA library in the expression vector λgt11 (R. A. Young and R. W. Davis, *Proc. Natl. Acad. Sci. USA* 80, 1194 (1983)) was produced as follows. The expression library was made from the DNA of the publically available 7G8 clone of the IMTM22 isolate of *P. falciparum* from Brazil.

Two 10 µg aliquots of genomic DNA from *Plasmodium falciparum* clone 7G8 were digested with 20 units of mung bean nuclease (P-L Biochemicals) for 30 min at 50° C. in 100 µl of buffer (0.2M NaCl, 1 mM ZnSO4, 30 mM sodium acetate, pH 4.6) containing either 35 or 40% formamide. The solution was then diluted 4-fold with 0.01M EDTA, extracted with phenol and ethanol precipitated before subsequent treatment. The DNA from the reactions were combined and used as a source of fragments to ligate in λgt11. The DNA was treated with Klenow fragment (BRL) under reaction conditions described (T. Maniatis, E. F. Fritsch and J. Sambrook, *Molecular Cloning: A Laboratory Manual*, Cold Spring Harbor Laboratory, N.Y., 1982, pg. 394) and EcoR1 linkers (BRL) wre blunt-end ligated to the treated fragments. The DNA was digested twice with an excess of EcoR1 and were separated from free linkers after each digestion on a 1.5 cm×20 cm Sepharose 4B column. λgt11 was self-ligated and digested with EcoRl. Two-hundred-thirty ng of the *P. falciparum* DNA fragments were ligated to 500 ng of the prepared λgt11 DNA overnight at 4° C. with T4 DNA ligase (IBI) under the conditions recommended by the supplier. One-half of the ligation reaction products were packaged into infectious phage in vitro (Promega Biotec). Four hundred thousand packaging events were scored by detectable interruption of the β-galactosidase gene of λgt11 on RY1090 growing on LB agar supplemented with Xgal and IPTG.

The library was plated at a density of 25,000 plaques per 150 mm plate on 27 plates; nitrocellulose plaque lifts were prepared as described previously (R. A. Young and R. W. Davis *Science* 222, 778, 1983). A pool of five monoclonal antibodies directed against the *P. falciparum* 7G8 CS protein (Table 1) was used at a dilution of 1/10,000 for screening.

TABLE 1

Reaction of anti-CS protein monoclonal antibodies with lysates of bacteria expressing cloned CS protein gene.

| Antigen | Monoclonal antibody | | | | |
|---|---|---|---|---|---|
|  | 2E 6.4 | 2F 1.1 | 4D 9.1 | 4D 11.6 | 5G 5.3 |
| λmPf1 (2.3 kg)+ | 1.2++ | 1.3 | 1.7 | 1.5 | 1.9 |
| λmPf3 (2.3 kg) | 1.3 | 1.1 | 1.9 | 1.4 | 1.8 |
| λmPf5 (1.3 kb) | 1.1 | 0.9 | 1.5 | 1.2 | 1.4 |
| λmPf8 (1.3 kb) | 1.2 | 0.9 | 1.6 | 1.2 | 1.4 |
| λmPf11 (2.3 kb) | 1.1 | 0.9 | 1.6 | 1.3 | 1.4 |
| λmPf13 (1.3 kb) | 0.6 | 0.5 | 0.5 | 0.7 | 0.6 |
| λmPf15 (1.35 kb) | 1.1 | 1.1 | >2.0 | 1.7 | >2.0 |
| λgt11, IPTG induced | 0.5 | 0.5 | 0.4 | 0.6 | 0.4 |
| λgt11, not induced | 0.5 | 0.4 | 0.4 | 0.6 | 0.4 |
| Y1089 | 0.4 | 0.5 | 0.3 | 0.6 | 0.3 |

+ λmPf, *P. falciparum* CS protein genes in λgt11. The size of the *P. falciparum* DNA insert in λgt11 is in parentheses. All bacteria were induced with IPTG.
++ The data are expressed as the mean absorbance at 414 nm for three independent determinations of ELISA.

Bacteria listed in Table 1 were identified by the following screening procedure. Pooled ascitic fluids of five hybridomas were diluted 1/10,000 in 0.15 m NaCl, 0.05M Tris, pH 7.5 (TBS) containing 0.05% Tween-20 and 3% BSA and was absorbed multiple times with a concentrated lysate of λgt11-infected RY1090 cells air dried onto nitrocellulose filters to remove antibodies to *E. coli* and lambda. Nitrocellulose plaque lifts from the *P. falciparum* library were washed in 500 ml of TBS, containing 0.3% Tween-20, 3% bovine serum albumin, 5 mM MgCl₂ and 5 µ/ml DNAse I at room temperature for 30 min. The nitrocellulose plaque lifts were incubated with the absorbed pool of monoclonal antibodies overnight at 4° C. All further manipulations were done at room temperature. After this and each of the next two steps, the plaque lifts were washed successively in TBS+0.05% Tween-20, in TBS+1% Triton X-100, and in TBS+0.5% Tween for 30 min in each solution. The signal of the mouse monoclonal antibodies was amplified by incubating the filters for 1 hr in rabbit anti-mouse IgG (Cappel) which had been diluted X500 in TBS containing 0.05% Tween and 3% BSA and preabsorbed as described above for the ascitic fluid. Antibodies bound to the plaque lifts were detected by incubating up to five filters in 30 ml of TBS containing a 0.05% Tween-20 and 1 µCi of $^{125}$I-labeled protein A (Amersham) followed by washing and autoradiography.

Thirty-five positive clones were obtained in the initial screening after 48 hrs of autoradiography. Seventeen were re-screened at a density of 100–800 plaques per 85 mm plate. Eleven of the clones gave positive plaques on the second screening. These were cloned without immunoscreening from 85 mm plates containing fewer than 50 plaques; ten of the 11 clones were immunoreactive when screened.

Inserts in the ten clones fell into the following size classes: three (λmPf1, 3, 11) were 2.3 kb, three (λmPf5, 8, 13) were 2.3 kb, λmpf15 was 1.35 kb, λmPf6 was 1.0 kb and λmPf9 was 0.5 kb. Clone λmPf18 contained two inserts and was not studied further. The inserts of clones λmPf1, 3, 5, 8, 11, 13 and 15 cross-hybridized. λmPf6 and 9 did not cross-hybridize, indicating that the two smaller inserts, although selected by the mixture of five monoclonal antibodies, came from a part of the genome outside the 2.3 kb fragment.

Clone λmPf5 was nick-translated and used to probe a Southern blot (E. M. Southern, *J. Mol. Biol.* 98, 503 (1975)) of Hind III digests of human and *P. falciparum* genomic DNA. A single band of hybridization was present at 14 Kb in the *P. falciparum* lane (data not shown). The probe did not hybridize to human DNA.

Expression of the CS Protein in *E. coli*

The clones in λgt11 were introduced as lysogens into *E. coli* strain Y1089. To produce lysogens, 10 μl of bacteriophage ($10^{10}$/ml) were mixed with 100 μl of *E. coli* Y1089 ($10^8$/ml) grown in media containing 50 μg/ml ampicillin and 0.2% maltose, pelleted and resuspended in 10 mM MgSO$_4$. After 20 min. at room temperature, the cells were diluted and spread onto plates containing 50 μg/ml ampicillin and grown at 32°. Individual colonies were tested for lysogeny by their inability to grow at 42°. Lysogens were grown in media containing 50 μg/ml ampicillin at 32° until the absorbance at 550 nm was 0.4–0.8. The cultures were then shaken gently at 44° for 20 min. IPTG was the added to a final concentration of 2 mM and the culture was shaken an additional 1 h at 37°. The phage were introduced at 44° C. and then isopropylthiogalactoside (IPTG) was added to the media to enhance expression of β-galactosidase and possible fusion proteins. Lysates of the induced bacteria were analyzed for reactivity with each of the five monoclonal antibodies by the enzyme linked immunosorbent assay (ELISA). Cells from 50 ml cultures that were grown and induced as described above were resuspended in 1.0 ml of 150 mM NaCl, 50 mM Tris-HCl, pH 8.0, 0.2 mM phenylmethylsulfonyl fluoride per 0.6 absorbance at 550 nm. Suspensions were quick frozen in a dry ice-ethanol bath and thawed two times before diluting with PBS. Lysates of clones were diluted 1/100 with phosphate buffered saline (PBS, 10 mM sodium phosphate, 150 mM NaCl). 50 μl aliquots were pipetted into wells of a polyvinyl chloride microtitration plate (Dynatech Laboratories, Inc., Alexandria, VA) and held at room temperature. Approximately 18 hours later, wells were washed four times with 0.1% (w/v) bovine serum albumin in PBS (PBS-BSA). Wells were then filled with 1% PBS-BSA and held 1 hr. at room temperature. Fifty μl of ascitic fluid from one of five separate monoclonal antibodies was diluted 1/500 with PBS, added to the appropriate well and held for 1 hour at room temperature. Ascitic fluids from these five monoclonal antibodies were positive in immunofluorescent antibody (IFA) and circumsporozoite precipitation (CSP) reactions for *P. falciparum* sporozoites. Wells were again washed as above and 50 μl of peroxidase conjugated goat anti-mouse antibody (Kirkegard & Perry Laboratories, Inc., Gaithersburg, MD) diluted 1/200 with PBS was added to each well and maintained at room temperature for 1 hour. Wells were washed with PBS-BSA and 150 μl of substrate was added to each well. The substrate consisted of 1 mg 2,2'-azino-di-(3-ethylbenzthiazoline sulfonic acid) per ml of 0.1M citrate-phosphate buffer, pH 4,0, with 0.003% hydrogen peroxide added immediately before use. Absorbance at 414 nm was determined at 1 hour with a Titertek Multiskan plate reader (Flow Laboratories, Inc., McLean, ZA). Six clones bound all five monoclonal antibodies (Table 1). The absorbance values for clone λmPf13 were not significantly above controls. Clone λmPf9 only bound one of the five monoclonal antibodies, 4D11.6 (data not shown). Since clone λmPf9 did not hybridize with λmPf1 which contains the gene for the CS protein (see below), this monoclonal antibody has identified a gene unrelated to the gene for the CS protein. The protein expressed by λmPf9 has an epitope cross-reactive with this one monoclonal antibody. Hope et al identified a monoclonal antibody to an asexual erythrocytic antigen of *P. falciparum* that cross-reacted with an antigen on the surface of *P. falciparum* sporozoites. I. A. Hope, R. Hall, D. Z. Simmons, et al. *Nature*, 308, 191 (1984). Whether λmPf9 contains a gene coding for the protein described by Hope et al or another crossreactive protein is yet to be determined.

The lysates used for the ELISA were also electrophoresed on SDS-polyacrylamide gel (SDS-PAGE) and electroblotted onto nitrocellulose. Pelleted cells from 1 ml of each lysogen culture (see note 14) were dissolved in 200 μl of SDS gel sample buffer (3% SDS, 10% glycerol, 10 mM dithiothreitol, 62 mM Tris-HCl, pH 6.8) and heated at 95° C. for 5 min. *Plasmodium falciparum* sporozoites were isolated from the salivary glands of *An. freeborni* mosquitoes and preserved as pellets at −80° C. in PBS containing 0.2% ovalbumin. For antigen extraction, 450 μl of freshly prepared extraction buffer (0.5% NP40, 2 mM PMSF, 33 μg/ml leupeptin, 33 μg/ml antipain and 2 mg/ml bovine serum albumin in PBS) was added to a pellet of $4.5 \times 10^5$ sporozoites. The material was incubated at room temperature for 1 hr. with vigorous vortexing for 15–30 sec. every 10 min. The extracted sporozoites were pelleted by centrifugation at 13,000 g for 2 min. The supernatant was put in SDS sample buffer for electrophoresis.

Western blot analysis was performed using a modification of the method of Towbin et al (*Proc. Natl. Acad. Sci. USA*, 79, 4350, 1979). Proteins were separated by SDS-polyacrylamide gel electrophoresis (SDS-PAGE) according to the method of Laemmli (*Nature*, 277, 680, 1970) using a 4.5% stacking gel and an 8–12% gradient gel. The gels were washed twice with 200 ml of Towbin's buffer for 30 min. per wash. The proteins separated on SDS-PAGE were blotted onto a 0.22 μm nitrocellulose filter at a field strength of 8 volts per cm for 14–16 hr. at 4° C. Unreacted binding sites on the nitrocellulose were blocked by treatment of the filter with 5% BSA in PBS containing 0.05% Tween 20. The blot was then washed four times with 100 ml of PBS containing 0.05% Tween, 20 min. per wash. The filter was reacted with a pool of five monoclonal antibodies (2E6.4, 2F1.1, 4D9.1, 4D11.6, and 5G5.3) for 90 min. The pool of monoclonal antibodies was prepared by diluting ascitic fluids for each antibody 1:100,000 with PBS containing 0.05% Tween 20 and 20% fetal calf serum (dilution of total ascites fluid, 1:20,000). The blots were washed four times as before and then treated with $^{125}$I-labeled sheep anti-serum prepared against whole mouse antibody. THe radioiodinated antiserum was diluted to $2 \times 10^5$ CPM/ml with PBS containing 0.05% Tween 20 and 20% fetal calf serum. The filters were then washed four times as before and dried. Autoradiography was performed using Kodak XAR-2 film at −80° C.

The proteins on the nitrocellulose paper were identified by anti-sporozoite monoclonal antibodies. The anti-sporozoite monoclonal antibodies against the protein blots of λmPf1, 3, 5, 8, 11 and 13 bound to two doublets of M$_r$ 60,000/57,000 and 53,000/51,000 (not shown), although the intensity for λmPf13 was greatly reduced. No binding occurred to the λgt11 vector without an insert. Monoclonal antibodies bound to proteins from sporozoites at $M_r$ 60,000, 53,000 and 51,000. Thus, all the sporozoite genes for CS protein in λgt11 produced a protein of similar mobility to the unprocessed CS protein synthesized by the sporozoite itself (~$M_r$ 60,000).

On induction with IPTG, a marked increased in expression of β-galactosidase $M_r$ of 116,000) was noted for λgt11 and a fusion protein at $M_r$ 131,000 with β-galactosidase was noted for λmPf9 (data not shown). The clones with the CS protein gene gave only weak β-galactosidase bands on introduction; no fusion proteins were seen (data not shown). In addition anti-β-galactosidase did not bind to the $M_r$ 60,000 CA protein, suggesting that this protein did not contain fragments of β-galactosidase (data not shown).

Figure 1:
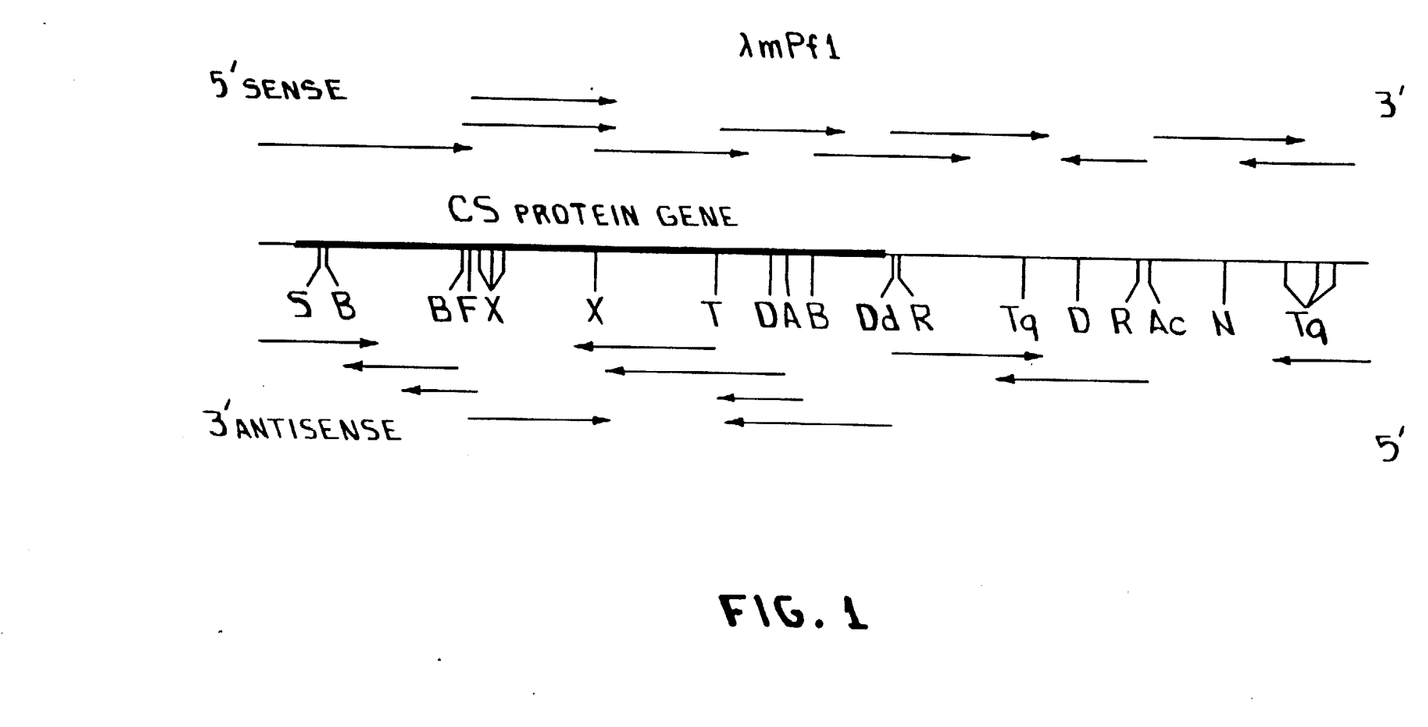
FIG. 1 shows a schematic restriction map and sequencing strategy of clone λmPf1. The positions of restriction enzyme cleavage sites shown in the figure were determined from the sequence and confirmed by digestion: A, AvaII; Ac, AccI; B, BstnI; D, DraI; Dd, DdeI; F, FokI; N, NdeI; R, RsaI; S, StuI; T, TthIII; Tq, TaqI; X, XhoII. Arrows indicate the origin, direction and extent of the sequences determined. The CS protein coding region is shown as a heavy line.

The λgt11 vector is designed to express inserts as β-galactosidase fusion proteins on induction with IPTG. Thus it was unexpected that none of the clones expressing the CS protein appeared to be fusion proteins. This is eplained for λmPf1, 5, 8 and 15 because the inserts are oriented so that their direction of transcription is opposite to that of β-galactosidase. Restriction mapping of the phage DNA using StuI, KpnI and StuI+KpnI indicate that the assymetric StuI site in the insert (FIG. 1) is located in each case ~1.1 kb from the KpnI site in λgt11 at 18.58 kb from the left end. It is not known whether the P. falciparum DNA 5' to the coding sequence in clones λmPf1 and 15 contains sequences that can be used as promoters by the E. coli RNA polymerase, but no obvious binding sites exist for bacterial ribosomes (FIG. 2). Clones λmPf5 and 8 begin only 11 bp before the gene. Thus, it is probable that expression of the CS protein in these clones is from a late lambda promoter. A similar phenomenon was observed in the λgt11 system with a yeast DNA insert. T. Goro and J. C. Wang, Cell, 36, 1073 (1984).

Restriction mapping indicates that the insert in λmPf13 is in the correct orientation with the β-galactosidase gene. However, it is one base out of frame to produce a fusion protein with β-galactosidase (FIG. 2). The low levels of CS protein produced by this clone as detected on Western blotting and its failure to give significant data in the ELISA (Table 1) may be understood in light of this construction. The bias among the clones for either reversed orientation or out of frame inserts suggests that there is selection against the expected fusion proteins (e.g., λmPf5 and 8 in the correct orientation), perhaps due to a toxic effect of the CS protein on E. Coli.

Structure of the P. falciparum Gene for the Circumsporozoite Protein

The nucleotide sequence of the 2.3 kb DNA fragment cloned in βmPf1 which contains the gene coding for the CS protein of P. falciparum is presented in FIG. 2. The deducted amino acid sequence for the protein is shown below the nucleotide sequence. A restriction map of the λmPf1 clone and the sequencing strategy is described in FIG. 1. This sequence contains a large open reading frame which commences with an ATG initiation codon at position 78 and terminates with a TAG codon at position 1316. Multiple terminator codons were observed in the other five reading frames. The open reading frame shown in FIG. 1 could code for a polypeptide of 412 amino acids with an approximate molecular mass of 44,000 daltons. As was observed for the CS protein of P. knowlesi, the molecular weight of the CS protein of P. falciparum by SDS-PAGE (~60,000) differed from the deduced molecular weight (44,000).

An important structural feature of this protein is the presence of 41 tandem repeats of tetrapeptides. The primary repeating unit is Asn-Ala-Asn-Pro which occurs 37 times; an alternate form is Asn-Val-Asp-Pro which occurs at units 2, 4, 6 and 22. The change from Ala-Asn to Val-Asp results from point mutations where C is replaced by T in the second position of the alanine codon and where A is replaced by G in the first position of the aspargine codon.

The nucleic acid sequence coding for the repeats is not as well conserved as the amino acid sequence. The repeated region which has 41 units is composed of 11 different combinations of nucleotide sequence. Eighteen of the units are of one type (AATGCAAACCCA). Seven of the repeats differs in only one position from this sequence, 12 differ in two positions, two differ in three positions, one differs in four positions, and one differs in five positions. The alteration in the sequence may stabilize the repeat within the genomic DNA from being eliminated or reshuffled by recombination.

At the amino terminal end of the protein, a stretch of 16 amino acids constitutes a probable signal sequence (FIG. 2). Between this signal sequence and the repeated region occurs a highly charged region which is characterized by the presence of both basic and acidic amino acids. Thus, 27 of 53 amino acids from amino acid 66 to amino acid 118 are charged amino acids.

Following the repeat region, two other segments of the protein contain a high proportion of charged amino acids. These regions occur between amino acids 324 and 339 and between amino acids 360 and 388; they contain 50% and 48% charged amino acids, respectively. At the carboxyl terminal end, the protein has a sequence of 21 hydrophobic amino acids which represents an anchor sequence for an integral membrane protein.

Immunoreactivity of Synthetic Peptides with Antibodies to the Repeat Sequence To prove conclusively that the releating nucleotide unit of the P. falciparum sporozoite gene was correct, peptides were synthesized. The peptides were prepared by the solid-phase method of peptide synthesis (R. B. Merrifield, and A. Marglin (1979) Annu. Rev. Biochem., 39, 841–866) using a.Beckman 990 peptide synthesizer. The synthetic peptides were cleaved from the solid support with liquid HF (J. P. Tam, W. F. Heath, and R. B. Merrifield, J. Am. Chem. Soc., 105, 6442) 1983. The cleaved peptides were desalted by gel filtration on Bio Gel P-2 or P-4. The purity of the isolated peptides was verified by reverse phase HPLC, amino acid analysis and, for the fifteen residue peptide, amino acid sequence analysis.

These peptides were then used in a modification of the ELISA assay described above to determine if they would inhibit binding of the monoclonal antibody 2F1.1 to λmPf1. The synthesis peptides were tested as follows. Fifty μl aliquotes of the λmPf1 lyusate (14) diluted 1/100 with 0.01M phosphate in 0.15M NaCl, pH 7.4 (PBS), were pipetted into wells of a polyvinyl chloride microtitration plate (Dynatech Laboratories, Inc., Alexandria, VA) and held overnight at room temperature. Approximately 18 hours later wells were washed four times with PBS-0.05% Tween 20 (PBS-TW), filled with 1.0% bovine serum albumin (BSA) in PBS-TW and held for 1 hour at room temperature. Stock solutions of synthetic peptides dissolved in distilled water ($5\times10^{-2}$M) were diluted 1/10 with 1% BSA in PBS and 100 µl aliquots mixed with 30 µl of monoclonal antibody 2F1.1 conjugated to horseradish peroxidase in 1.5 ml microcentrifuge tubes and held for 1 hour at room temperature. Wells of the microtitration plate were emptied and 30 µl of the peptide-monoclonal antibody mixture placed in each well and held for 1 hour at room temperature. Wells were again washed as above and 150 µl of substrate added as previously described (P. K. Nakane and A. Kawzaoi, *J. Hist. Cytochem.*, 11, 1084, 1974).

Figure 3:
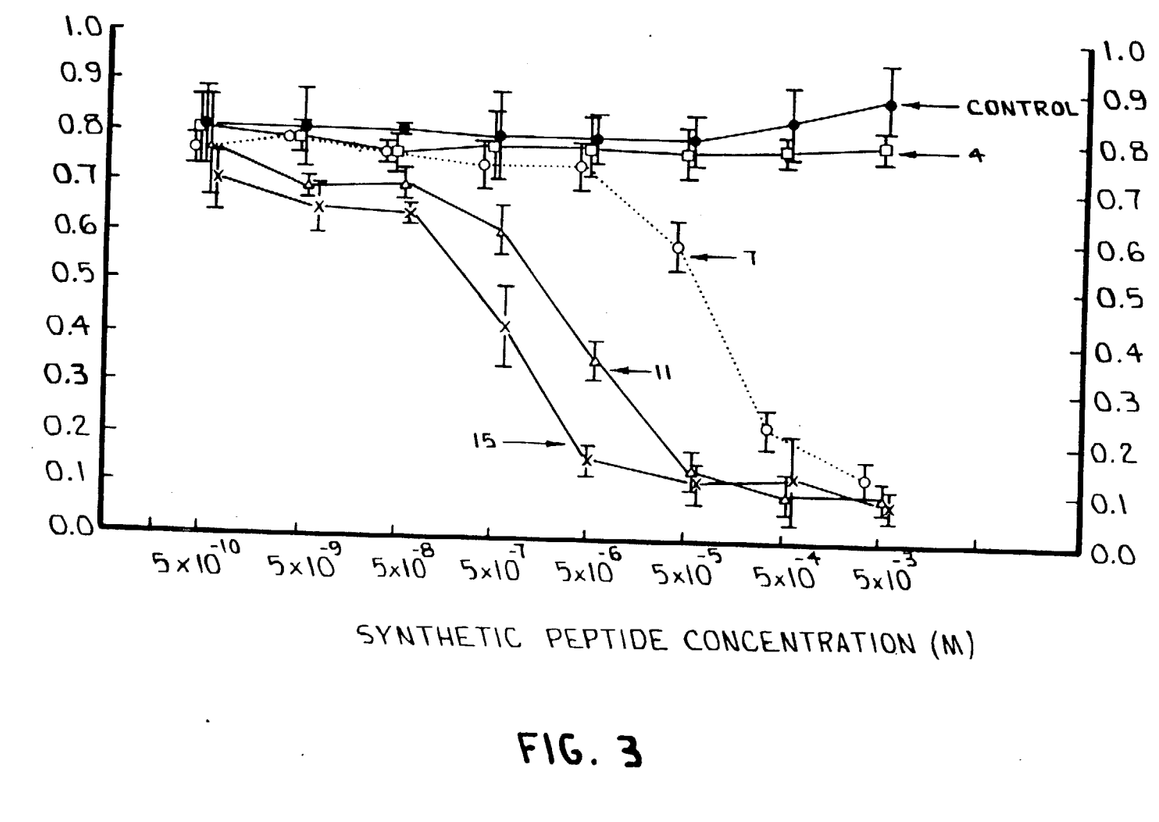
FIG. 3 presents, in graphical form, data showing inhibition of binding of anti-CS protein monoclonal antibody, 2F1.1, by synthetic peptides of the predominant repeating amino acid sequence. Synthetic peptides containing increasing lengths of the predominant repeat sequence were prepared and utilized to inhibit binding of 2F1.1 to a lysate of λmPf1 growing in Y1089. The data are given as the mean ±SE of three replicates. The synthetic sequences tested were Asn-Pro-Asn-Ala (□—□), Pro-Asn-Ala-Asn-Pro-Asn-Ala (○—○), Pro-Asn-Ala-Asn-Pro-Asn-Ala-Asn-Pro-Asn-Ala (△—△), Pro-Asn-Ala-Asn-Pro-Asn-Ala-Asn-Pro-Asn-Ala-Asn-Pro-Asn-Ala (x—x), and an unrelated decapeptide (•—•).

The results shown in FIG. 3 demonstrate that the 7, 11, and 15 residue peptides significantly inhibit binding of 2F1.1 to λmPf1. Inhibition of binding was evident at $5\times10^{-7}$M with the 15 residue peptide. The 7 residue peptide also inhibited binding of monoclonal antibody 2F1.1 to the sporozoite antigen substituted for λmPf1 (data not shown). Furthermore, the synthetic peptide inhibited binding of the other four monoclonal antibodies to λmPf1. These data indicate that the sequence of the repeating unit is correct. The increased inhibition of binding seen with the 11 and 15 residue peptides may reflect secondary conformational changes. The data do not suggest that they contain two epitopes since neither could be detected in a double-sided assay with 2F1.1 (data not shown).

Regions of Homology Between CS Proteins of P. falciparum and P. knowlesi

The CS protein of *P. falciparum* and the CS protein of a monkey malaria, *P. knowlesi*, have a similar overall structure, but have only two short regions of homology. Both proteins appear to contain the same major features in that they have a repeated region in the middle of the protein, multiple regions with a high density of charged amino acids a signal sequence at the amino terminal end, and a hydrophobic anchor sequence at the carboxyl terminal end. However, computer analysis for the amino acid sequence homology (25, K tuple size of 1, window size of 20, gap penalty of 1) found limited sequence homology over most of the protein. The average homology between the two proteins in the segment before the repeat is 37%; 37 of a possible 102 amino acids match. The repeats share 16% homology since one Pro and one Ala align every 12 amino acids. The average homology between the segments of the two proteins after the repeats is 42%; 50 of a possible 119 amino acids match. As the secondary and tertiary structure of these proteins are unknown, they may have structural and functional similarities despite the difference in primary sequence. For example, repeats in CS proteins are immunodominant following vaccination with sporozoites.

The two regions of greatest sequence homology were seen on either side of the repeated regions. When the two peptides are aligned a region of homology is apparent where three prolines are aligned and a perfect match of five contiguous amino acids (Lys-Leu-Lys-Gln-Pro) occurs (Region I, FIGS. 2 and 4*a*).

The second region of homology (Region II, FIGS. 2 and 4*b*) contains 13 amino acids, 12 of which are conserved. The only amino acid that was not identical was the substitution of threonine for serine at the fourth residue in the *P. knowlesi* sequence. This region contains two cysteine residues which were implicated earlier by Ozaki et al. L. S. Ozaki, P. Svec, R. S. Nussenzweig, et al. *Cell* 34, 815 (1983), in the formation of an intramolecular loop.

The nucleic acid sequence encoding the CS protein of *P. falciparum* also has limited homology with the *P. knowlesi* gene except in Region II. In the portion of the gene encoding Region II of the protein, a 27 base sequence is present which differs from the comparable sequence in *P. knowlesi* at only two positions. This conserved sequence may be useful as a probe to clone the genes encoding the CS proteins of the other Plasmodium species.

These two regions of homology of amino acid sequence between *P. falciparum* and *P. knowlesi* indicate conservation of sequence for organisms widely separated in evolution. It was originally assumed that the primate malarias had evolved in parallel with the evolution of primates. Recently, however, it has been demonstrated that the DNA of *P. falciparum* is similar to the DNA of avian and rodent malarias and that these had a different DNA structure than the primate malarias (*P. knowlesi, P. fragile, P. vivax* and *P. cynomolgi*); *P. falciparum, P. lophurae* and *P. berghei* had a lower G+C content than the primate malarias including *P. knowlesi*. In addition, gene probes that hybridized to *P. falciparum, P. lophurae,* and *P. berghei* DNAs did not hybridize to the primate malarias and probes that hybridized to the primate malarias did not hybridize to *P. falciparum, P. lophurae* and *P. berghei*. This region of homology between *P. falciparum* and *P. knowlesi* may be conserved for an important function of the protein such as reception for cell invasion. It should be noted that both *P. falciparum* and *P. knowlesi* sporozoites can infect the human liver.

Figure 4A:
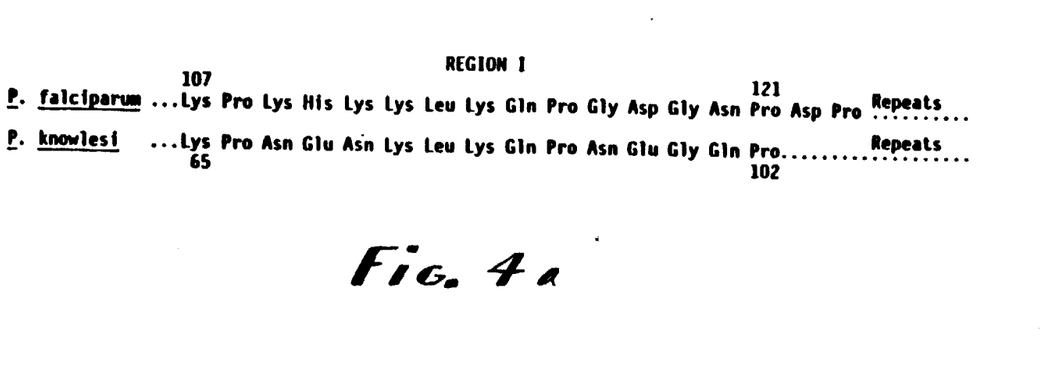
FIGS. 4a and 4b show formulas of regions of homology beween the CS proteins of P. falciparum and P. knowlesi. Region I ends two amino acids from the repeat portion of the protein in P. falciparum. In P. knowlesi the last 3 amino acids of this region are part of the repeating portion of the protein.
Figure 4B:
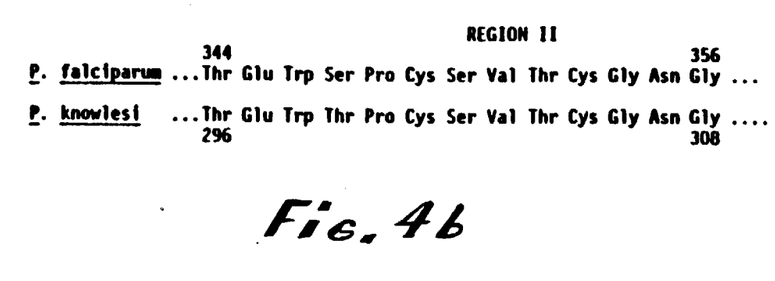

Despite the potential problem of shared epitopes among proteins, considerable evidence shows that the sporozoite gene has been cloned. First, the similarity between this protein of *P. falciparum* and the CS protein of *P. knowlesi* is striking. Both are of similar size with calculated molecular weights of 44,426 and 36,792 for *P. falciparum* and *P. knowlesi*, respectively. Both have analogous regions that include a signal sequence, charged region, a region of repeating peptides in the middle of the protein and an anchor sequence. Second, there are two regions of amino acid homology between the two proteins (FIG. 4). Third, five monoclonal antibodies known to react with the surface of *P. falciparum* sporozoites (11) recognized the protein synthesized in the bacteria. The cross-reactive protein from clone λmPf9 only reacted with one of these monoclonal antibodies. Fourth, the protein synthesized in bacteria was of similar size in SDS-PAGE to the protein from *P. falciparum* sporozoites. Fifth, synthetic peptides of the repeat blocked binding of a monoclonal antibody to the sporozoite protein in an ELISA.

The gene encodes a protein of 412 amino acids which consist of a signal sequence, a charged region, a central region of 41 fourth amino acid units (repeats), two other charged regions, a probable cystine loop and an anchor sequence. Thirty-seven of the repeats in the central region are identical (Asn-Ala-Asn-Pro); four have an alternate sequence (Asn-Val-Asp-Pro).

An analogous set of CS proteins are found on sporozoites of all Plasmodium species studied to date. Monoclonal antibodies to CS proteins confer protection in vivo or neutralize sporozoite infectivity in vitro. A. H. Cochrane, F. Santoro, V. Nussenzweig et al, *Proc. Natl. Acad. Sci. USA,* 79, 5651 (1982). Although monoclonal antibodies may cross react among species of primate malaria, antibody mediated immunity appear to be species specific, and in the case of *P. knowlesi* protective monoclonal antibodies are directed against the repeating epitope. These data and the finding that monoclonal antibodies to sporozoites react in an assay that requires two or more epitopes led Zavala et al. to propose that monoclonal antibodies to CS proteins react with an immunodominant region that has a repeating epitope. This hypothesis has been confirmed in that the five monoclonal antibodies to the CS protein of *P. falciparum* are directed against repeating units, (Asn-Ala-Asn-Pro), in the protein.

The striking homology of Region II between two otherwise evolutionarily divergent malaria parasites, *P. falciparum* and *P. knowlesi* suggests conservation for a sporozoite function such as reception for liver invasion. If this region is conserved in other human malarias and is exposed to the immune system, immunization with this region from *P. falciparum* may give protection against other species of human malaria. Furthermore, if this homologous region is involved in reception for liver invasion, then the malarial parasite may be unable to vary the sequence in this region.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. An antimalarial immunogenic stimulant comprising an immunogenic carrier and a peptide sequence of between 2 and 1000 consecutive repeats of a sequence Asn-X-Y-Pro, wherein X is Ala or Val and Y is Asn or Asp.

2. The stimulant of claim 1, wherein said carrier forms at most 90% of said stimulant.

3. The stimulant of claim 1, wherein carrier forms at most 40% of said stimulant.

4. A peptide having a sequence A-B-A-B-A-B-(A)$_{15}$-B-(A)$_{20}$, wherein A represents Asn-Ala-Asn-Pro and B represents Asn-Val-Asp-Pro.

5. A peptide having a sequence A-B-A-B-A-B-(A)$_{15}$-B-(A)$_{20}$, wherein A represents Asn-Ala-Asn-Pro and B represents Asn-Val-Asp-Pro, wherein said sequence is followed by a peptide segment having a sequence Thr-Glu-Trp-Z-Pro-Cys-Ser-Val-Thr-Cys-Gly-Asn-Gly, wherein Z is Ser or Thr; or is preceded by a peptide segment having a sequence Lys-Pro-S-T-S-Lys-Leu-Lys-Gln-Pro-U-V-Gly-W-Pro, wherein S is Lys or Asn, T is His or Glu, U is Gly or Asn, V is Asp or Glu, and W is Asn or Gln.

6. The peptide of claim 5, wherein said peptide has a sequence Lys-Pro-Lys-His-Lys-Lys-Leu-Lys-Gln-Pro-Gly-Asp-Gly-Asn-Pro-Asp-Pro-Asn-Ala-Asn-Pro-Asn-Val-Asp-Pro-Asn-Ala-Asn-Pro-Asn-Val-Asp-Pro-Asn-Ala-Asn-Pro-Asn-Val-Asp-Pro-Asn-Ala-Asn-Pro-Asn-Ala-Asn-Pro-Asn-Ala-Asn-Pro-Asn-Ala-Asn-Pro-Asn-Ala-Asn Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Val-Asp-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-As -Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Ala-Asn-Pro-Asn-Lys-Asn-Asn-Gln-Gly-Asn-Gly-Gln-Gly-His-Asn-Met-Pro-Asn-Asp-Pro-Asn-Arg-Asn-Val-Asp Glu-Asn-Ala-Asn-Ala-Asn-Asn-Ala-Val-Lys-Asn-Asn-Asn-Asn-Glu-Glu-Pro-Ser-Asp-Lys-His-Ile-Glu-Gln-Tyr-Leu-Lys-Lys-Ile-Lys-Asn-Ser-Ile-Ser-Thr-Glu-Trp-Ser-Pro-Cys-Ser-Val-Thr-Cys-Gly-Asn-Gly.

7. A vaccine comprising an antimalarial immunogenic stimulant and a physiologically-compatible medium therefor, wherein said stimulant contains an immunogenic carrier and a peptide sequence Thr-Glu-Trp-Z-Pro-Cys-Ser-Val-Thr-Cys-Gly-Asn-Gly, wherein Z is Ser or Thr, or a peptide sequence Lys-Pro-S-T-S-Lys-Leu-Lys-Gln-Pro-U-V-Gly-W-Pro, wherein S is Lys or Asn, T is His or Glu, U is Gly or Asn, V is Asp or Glu, and W is Asn or Gln, and (b) is present in an amount sufficient to elicit an immune response against *Plasmodium falciparum*.

8. The vaccine of claim 7, wherein said carrier forms at most 90% of said peptide.

9. The vaccine of claim 8, wherein said sequence is Thr-Glu-Trp-Z-Pro-Cys-Ser-Val-Thr-Cys-Gly-Asn-Gly.

10. The peptide of claim 9 wherein Z is Ser.

11. The stimulant of claim 1, wherein said carrier is bonded to said sequence by an amide bond formed between a carboxylic acid or amino group of said carrier and an amino or carboxylic acid group of said sequence, or by an ester bond formed between a carboxylic acid or hydroxy group of said carrier and an hydroxy or carboxylic acid group of said sequence.

12. The stimulant of claim 1, wherein said carrier is a protein or a polysaccharide.

13. The stimulant of claim 12, wherein said carrier has a molecular weight of from 10,000 to 1,000,000.

14. The stimulant of claim 12 wherein said carrier is an amphoteric protein and said sequence is bound to the hydrophylic portion of said protein.

15. The stimulant of claim 1, wherein said carrier is a bacterial cell or a liposome.

16. A method for inducing immunization against malaria which comprises the step of administering an immunologically effective amount of a stimulant of claim 2 to a human.

17. The stimulant of claim 1, wherein said carrier forms at most 40% of said stimulant.

18. The stimulant of claim 1, wherein said carrier form at most 20% of said stimulant.

19. The stimulant of claim 18, wherein carrier forms up to 50% of said repeats.

20. The stimulant of claim 1, wherein said malaria parasite is *Plasmodium falciparum*.

21. A vaccine comprising an antimalarial immunogenic stimulant and a physiologically-compatible medium therefor, wherein said stimulant (a) contains an immunogenic carrier and between 2 and 1000 consecutive repeats of a sequence Asn-X-Y-Pro, wherein X is Ala or Val and Y is Asn or Asp, and (b) is present in an amount sufficient to elicit an immune response against *Plasmodium falciparum*.

22. The vaccine of claim 21, wherein said carrier forms at most 90% of said stimulant.

23. The vaccine of claim 7, wherein said immune response is against *Plasmodium falciparum* sporozoites.

24. The vaccine of claim 7, wherein said immunogenic carrier is a water-soluble macromolecule ranging in molecular weight between about 10,000 and 1,000,000.

25. A method for inducing immunization against malaria which comprises the step of administering to a human an immunologically effective amount of an antimalarial immunogenic.stimulant comprising an immunogenic carrier and a peptide sequence Thr-Glu-Trp-Z-Pro-Cys-Ser-Val-Thr-Cys-Gly-Asn-Gly, wherein Z is Ser or Thr, or a peptide sequence Lys-Pro-S-T-S-Lys-Leu-Lys-Gln-Pro-U-V-Gly-W-Pro, wherein S is Lys or Asn, T is His or Glu, U is Gly or Asn, V is Asp or Glu, and W is Asn or Gln.

26. The method of claim 25, wherein said carrier forms at most 90% of said stimulant.

27. The method of claim 26, wherein said stimulant consists essentially of said sequence and said carrier.

28. The method of claim 26, wherein said sequence is Thr-Glu-Trp-Z-Pro-Cys-Ser-Val-Thr-Cys-Gly-Asn-Gly.

29. The method of claim 28, wherein Z is Ser.

30. An immunologically active peptide consisting of between 2 and 1000 consecutive repeats of a sequence Asn-X-Y-Pro, wherein X is Ala or Val and Y is Asn or Asp.

* * * * *

UNITED STATES PATENT AND TRADEMARK OFFICE
CERTIFICATE OF CORRECTION

PATENT NO. : 4,707,357

DATED : November 17, 1987

INVENTOR(S) : John B. Dame, Jackie L. Williams, Thomas F. McCutchan, Imogene Schneider It is certified that error appears in the above-identified patent and that said Letters Patent is hereby corrected as shown below:

In Claim 3, column 19, line 37 of the patent, delete "40%" and substitute --60%-- therefor.

In Claim 6, column 19, line 62 of the patent, delete the letters "As" where they occur by themselves and substitute --Asn-- therefor.

In Claim 6, column 20, line 1 of the patent, delete the " " between "Asp" and "Glu" and substitute -- - -- therefor.

In Claim 7, column 20, line 8 of the patent, insert --(a)-- between "stimulant" and "contains".

In Claim 10, column 20, line 22 of the patent, delete "peptide" and substitute --vaccine-- ; after "9" insert a comma -- , --.

In Claim 16, column 20, line 42 of the patent, delete "2" and substitute --1-- therefor.

Signed and Sealed this

Fifth Day of July, 1988

*Attest:*

*Attesting Officer*

DONALD J. QUIGG

*Commissioner of Patents and Trademarks*